United States Patent
Simms et al.

(10) Patent No.: US 8,781,847 B2
(45) Date of Patent: Jul. 15, 2014

(54) SYSTEM AND METHOD FOR MANAGING ALERT NOTIFICATIONS IN AN AUTOMATED PATIENT MANAGEMENT SYSTEM

(75) Inventors: Howard D. Simms, Shoreview, MN (US); Kenneth P. Hoyme, Plymouth, MN (US); David C. Johnson, Inver Grove Heights, MN (US); Muralidharan Srivathsa, Shoreview, MN (US); James R. Kalgren, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1462 days.

(21) Appl. No.: 11/121,870

(22) Filed: May 3, 2005

(65) Prior Publication Data

US 2006/0253301 A1 Nov. 9, 2006

(51) Int. Cl.
G06Q 10/00 (2012.01)
G06Q 50/00 (2012.01)

(52) U.S. Cl.
CPC .................................... G06Q 10/00 (2013.01)
USPC ................................................. 705/2; 705/3

(58) Field of Classification Search
CPC .................................................... G06Q 10/00
USPC .............. 705/2–3; 600/300, 537; 379/106.02; 340/605; 709/224
See application file for complete search history.

(56) References Cited

U.S. PATENT DOCUMENTS

| | | | |
|---|---|---|---|
| 3,776,221 A | 12/1973 | McIntyre | |
| 3,837,339 A | 9/1974 | Aisenberg et al. | |
| 4,009,721 A | 3/1977 | Alcidi | |
| 4,142,533 A | 3/1979 | Brownlee et al. | |
| 4,197,856 A | 4/1980 | Northrop | |
| 4,531,527 A | 7/1985 | Reinhold, Jr. et al. | |
| 4,548,211 A | 10/1985 | Marks | |
| 4,686,999 A | 8/1987 | Snyder et al. | |
| 4,750,495 A | 6/1988 | Moore et al. | |
| 4,803,625 A | 2/1989 | Fu et al. | |

(Continued)

FOREIGN PATENT DOCUMENTS

| | | |
|---|---|---|
| EP | 0 342 859 | 11/1989 |
| EP | 0 513 457 | 11/1992 |

(Continued)

OTHER PUBLICATIONS

E. Braunwald, "Heart Disease—A Textbook of Cardiovascular Medicine," pp. 46-52 (5th Ed. 1997).

(Continued)

*Primary Examiner* — Joseph Burgess
(74) *Attorney, Agent, or Firm* — Pauly, DeVries Smith & Deffner, LLC (57) ABSTRACT

A system and method for managing alert notifications in an automated patient management system is presented. One or more settings specifying patient data collection periodicity are defined. One or more patient data sources operating on a remotely managed patient and selected from at least one of a physiological sensor and a therapy delivery device are also defined. One or more triggers associated with a condition occurring in relation to at least one such patient data evaluateable subsequent to collection are defined. Finally, a notification scheme executable upon detection of at least one such trigger is determined to provide an external indicator of the condition occurrence.

17 Claims, 7 Drawing Sheets

(56) References Cited

U.S. PATENT DOCUMENTS

| | | | |
|---|---|---|---|
| 4,809,697 A | 3/1989 | Causey, III et al. |
| 4,852,570 A | 8/1989 | Levine |
| 4,899,758 A | 2/1990 | Finkelstein et al. |
| 4,958,645 A | 9/1990 | Cadell et al. |
| 4,974,607 A | 12/1990 | Miwa |
| 4,987,897 A | 1/1991 | Funke |
| 5,003,976 A | 4/1991 | Alt |
| 5,040,536 A | 8/1991 | Riff |
| 5,113,859 A | 5/1992 | Funke |
| 5,113,869 A | 5/1992 | Nappholz et al. |
| 5,133,346 A | 7/1992 | Kulkarni |
| H1114 H | 12/1992 | Schweitzer et al. |
| 5,199,428 A | 4/1993 | Obel et al. |
| 5,291,895 A | 3/1994 | McIntyre |
| 5,301,105 A | 4/1994 | Cummings, Jr. |
| 5,331,549 A | 7/1994 | Crawford, Jr. |
| 5,336,245 A | 8/1994 | Adams et al. |
| 5,355,889 A | 10/1994 | Nevo et al. |
| 5,357,427 A | 10/1994 | Langen et al. |
| 5,390,238 A | 2/1995 | Kirk et al. |
| 5,416,695 A | 5/1995 | Stutman et al. |
| 5,421,343 A | 6/1995 | Feng |
| 5,437,278 A | 8/1995 | Wilk |
| 5,438,983 A | 8/1995 | Falcone |
| 5,464,012 A | 11/1995 | Falcone |
| 5,522,860 A | 6/1996 | Molin et al. |
| 5,544,661 A | 8/1996 | Davis et al. |
| 5,553,609 A | 9/1996 | Chen et al. |
| 5,557,514 A | 9/1996 | Seare et al. |
| 5,576,952 A | 11/1996 | Stutman |
| 5,584,868 A | 12/1996 | Salo et al. |
| 5,591,215 A | 1/1997 | Greenhut et al. |
| 5,603,331 A | 2/1997 | Heemels et al. |
| 5,660,183 A | 8/1997 | Chiang et al. |
| 5,673,691 A | 10/1997 | Abrams et al. |
| 5,687,734 A | 11/1997 | Dempsey et al. |
| 5,697,959 A | 12/1997 | Poore |
| 5,704,345 A | 1/1998 | Berthon-Jones |
| 5,704,366 A | 1/1998 | Tacklind et al. |
| 5,711,297 A | 1/1998 | Iliff |
| 5,713,350 A | 2/1998 | Yokota et al. |
| 5,720,770 A | 2/1998 | Nappholz et al. |
| 5,720,771 A | 2/1998 | Snell |
| 5,724,580 A | 3/1998 | Levin et al. |
| 5,724,983 A | 3/1998 | Selker et al. |
| 5,738,102 A | 4/1998 | Lemelson |
| 5,743,267 A | 4/1998 | Nikolic |
| 5,749,907 A | 5/1998 | Mann |
| 5,749,908 A | 5/1998 | Snell |
| 5,752,976 A | 5/1998 | Duffin et al. |
| 5,769,074 A | 6/1998 | Barnhill et al. |
| 5,772,586 A | 6/1998 | Heinonen et al. |
| 5,772,599 A | 6/1998 | Nevo et al. |
| 5,772,604 A | 6/1998 | Langberg et al. |
| 5,778,882 A | 7/1998 | Raymond et al. |
| 5,785,650 A | 7/1998 | Akasaka et al. |
| 5,785,660 A | 7/1998 | Van Lake et al. |
| 5,788,640 A | 8/1998 | Peters |
| 5,788,643 A | 8/1998 | Feldman |
| 5,792,062 A | 8/1998 | Poon et al. |
| 5,819,251 A | 10/1998 | Kremer et al. |
| 5,855,593 A | 1/1999 | Olson et al. |
| 5,860,918 A | 1/1999 | Schradi et al. |
| 5,876,353 A | 3/1999 | Riff |
| 5,879,375 A | 3/1999 | Larson, Jr. et al. |
| 5,891,178 A | 4/1999 | Mann et al. |
| 5,897,493 A | 4/1999 | Brown |
| 5,911,132 A | 6/1999 | Sloane |
| 5,931,857 A | 8/1999 | Prieve et al. |
| 5,954,640 A | 9/1999 | Szabo |
| 5,957,861 A | 9/1999 | Combs et al. |
| 5,974,124 A | 10/1999 | Schlueter, Jr. et al. |
| 5,987,352 A | 11/1999 | Klein et al. |
| 5,993,386 A | 11/1999 | Ericsson |
| 6,004,276 A | 12/1999 | Wright et al. |
| 6,014,581 A | 1/2000 | Whayne et al. |
| 6,024,699 A | 2/2000 | Surwit et al. |
| 6,038,469 A | 3/2000 | Karlsson et al. |
| 6,047,203 A | 4/2000 | Sackner et al. |
| 6,050,940 A | 4/2000 | Braun |
| 6,063,028 A | 5/2000 | Luciano |
| 6,067,466 A | 5/2000 | Selker et al. |
| 6,073,046 A | 6/2000 | Patel |
| 6,074,345 A * | 6/2000 | van Oostrom et al. ........ 600/300 |
| 6,080,106 A | 6/2000 | Lloyd et al. |
| 6,083,248 A | 7/2000 | Thompson |
| 6,093,146 A | 7/2000 | Filangeri |
| 6,095,985 A | 8/2000 | Raymond et al. |
| 6,102,856 A | 8/2000 | Groff et al. |
| 6,120,442 A | 9/2000 | Hickey |
| 6,122,351 A | 9/2000 | Schlueter, Jr. et al. |
| 6,129,675 A | 10/2000 | Jay |
| 6,132,384 A | 10/2000 | Christopherson et al. |
| 6,135,951 A | 10/2000 | Richardson et al. |
| 6,139,494 A | 10/2000 | Cairnes |
| 6,152,882 A | 11/2000 | Prutchi |
| 6,155,267 A | 12/2000 | Nelson |
| 6,168,563 B1 | 1/2001 | Brown |
| 6,168,653 B1 | 1/2001 | Myers |
| 6,171,237 B1 | 1/2001 | Avitall et al. |
| 6,171,256 B1 | 1/2001 | Joo et al. |
| 6,223,078 B1 | 4/2001 | Marcovecchio |
| 6,225,901 B1 | 5/2001 | Kail, IV |
| 6,234,964 B1 | 5/2001 | Iliff |
| 6,238,349 B1 | 5/2001 | Hickey |
| 6,246,992 B1 | 6/2001 | Brown |
| 6,249,705 B1 | 6/2001 | Snell |
| 6,250,309 B1 | 6/2001 | Krichen et al. |
| 6,263,245 B1 | 7/2001 | Snell |
| 6,283,923 B1 | 9/2001 | Finkelstein et al. |
| 6,287,252 B1 | 9/2001 | Lugo |
| 6,290,646 B1 | 9/2001 | Cosentino et al. |
| 6,302,844 B1 | 10/2001 | Walker et al. |
| 6,306,088 B1 | 10/2001 | Krausman et al. |
| 6,336,900 B1 | 1/2002 | Alleckson |
| 6,363,282 B1 | 3/2002 | Nichols et al. |
| 6,416,471 B1 | 7/2002 | Kumar et al. |
| 6,428,483 B1 | 8/2002 | Carlebach |
| 6,442,433 B1 | 8/2002 | Linberg |
| 6,454,705 B1 | 9/2002 | Cosentino et al. |
| 6,463,326 B1 | 10/2002 | Hartley et al. |
| 6,477,424 B1 | 11/2002 | Thompson et al. |
| 6,512,949 B1 | 1/2003 | Combs et al. |
| 6,662,032 B1 | 12/2003 | Gavish et al. |
| 6,795,733 B1 | 9/2004 | Lu |
| 6,827,670 B1 | 12/2004 | Stark et al. |
| 6,839,753 B2 * | 1/2005 | Biondi et al. .................. 709/224 |
| 6,904,320 B2 | 6/2005 | Park et al. |
| 7,104,955 B2 | 9/2006 | Bardy |
| 7,252,640 B2 | 8/2007 | Ni et al. |
| 2002/0016719 A1* | 2/2002 | Nemeth et al. ..................... 705/2 |
| 2002/0082480 A1* | 6/2002 | Riff et al. ...................... 600/300 |
| 2002/0123674 A1 | 9/2002 | Plicchi et al. |
| 2002/0138017 A1* | 9/2002 | Bui et al. ...................... 600/537 |
| 2002/0181680 A1* | 12/2002 | Linder et al. ............. 379/106.02 |
| 2003/0055679 A1 | 3/2003 | Soll et al. |
| 2003/0128126 A1* | 7/2003 | Burbank et al. .............. 340/605 |
| 2004/0103001 A1 | 5/2004 | Mazar et al. |
| 2004/0117204 A1 | 6/2004 | Mazar et al. |
| 2004/0158132 A1 | 8/2004 | Zaleski |
| 2005/0055242 A1 | 3/2005 | Bello et al. |
| 2005/0065567 A1 | 3/2005 | Lee et al. |
| 2006/0017575 A1* | 1/2006 | McAdams .................. 340/573.1 |
| 2006/0020491 A1* | 1/2006 | Mongeon et al. ..................... 705/2 |
| 2006/0122469 A1* | 6/2006 | Martel ......................... 600/300 |

FOREIGN PATENT DOCUMENTS

| | | |
|---|---|---|
| EP | 0 531 889 A2 | 3/1993 |
| EP | 0 711 531 A1 | 5/1996 |
| JP | 2002298245 | 10/2002 |
| JP | 2001325355 | 11/2011 |
| WO | WO 97/39792 | 10/1997 |
| WO | WO 98/07142 | 2/1998 |

(56) References Cited

FOREIGN PATENT DOCUMENTS

| WO | WO 98/42103 | 9/1998 |
|----|----|----|
| WO | WO-9841271 | 9/1998 |
| WO | WO 99/46718 | 9/1999 |
| WO | WO 99/55226 | 11/1999 |
| WO | WO 01/97703 | 12/2001 |
| WO | WO-2004070994 | 8/2004 |

OTHER PUBLICATIONS

Hamilton et al., "Arterial, Cerebrospinal and Venous Pressures in Man During Cough and Strain," 144 Am. J. of Phys., pp. 42, 42-50 (1944).

Zema et al., "Left Ventricular Dysfunction—Bedside Valsalva Maneuver," Br. Heart J., pp. 44:560-569 (1980).

McKay et al., "Instantaneous Measurement of Left and Right Ventricular Stroke Volume and Pressure-Volume Relationships with an Impedance Catheter," Circ. 69, No. 4, pp. 703-710 (1984).

Wortel et al., "Impedance Measurements in the Human Right Ventricle Using a New Pacing System," Pacing Clinical Electrophysiology, vol. 14(9), pp. 1336-1342 (Sep. 1991).

Seborg et al., "Process Dynamics and Control," pp. 165-167, John Wiley & Sons (1989).

Dunn et al., "Telemedicine Links Patients in Sioux Lookout with Doctors in Toronto," CMA Journal, vol. 122, pp. 484-487 (Feb. 23, 1980).

Auer et al., "Paced Epimyocardial Electrograms for Noninvasive Rejection Monitoring After Heart Transplantation," The Journal of Heart and Lung Transplantation, vol. 15, No. 10, pp. 993-998 (Oct. 1996).

Schreier et al., "A Non-Invasive Rejection Monitoring System Based on Remote Analysis of Intramyocardial Electrograms from Heart Transplants," IEEE, pp. 35-36 (1997).

Roberge et al., "Basic and Applied Biomedical Engineering Building Blocks for Health Care," 1995 IEEE Engineering in Medicine and Biology 17th Annual Conference, vol. 1, 1995). Montreal—Canada, (Sep. 20-23, 1995).

Hutten et al., "Cardiac Telemonitoring by Integrating Pacemaker Telemetry within Worldwide Data Communication Systems," Proceedings of 19th International Conference, IEEE/EMBS, Chicago, IL, pp. 974-976 (Oct. 30-Nov. 2, 1997).

Vargas, Juan E., "Home-Based Monitoring of Cardiac Patients," Dept. of Electr. & Comput. Eng., South Carolina Univ., Columbia, SC, Information Technology Applications in Biomedicine, Proceedings., 1998 IEEE International Conference, pp. 133-136 (May 16-17, 1998).

Magrabi et al., "Web Based Longitudinal ECG Monitoring," Proceedings of 20th Annual International Conference of the IEEE Engineering in Medicine and Biology Society, vol. 20, No. 3, pp. 1155-1158 (1998).

Nelwan et al., "Ubiquitous Access to Real-Time Patient Monitoring Data," Computers in Cardiollogy., vol. 24, pp. 271-274 (1997).

Moody GB, "Integration of Real-Time and Off-Line Clinical Data in the MIMIC Database," Computers in Cardiology 1997 vol. 24, pp. 585-588, Cambridge, MA USA.

Long WJ, et al., "Differential Diagnosis Generation From a Causal Network With Probabilities," Computers in Cardiology, 1988, Proceedings, pp. 185-188, Washington DC, USA.

Health Insurance Portability and Accountability Act of 1996, Pub. L. No. 104-191, 110 Stat. 1936 (Aug. 21, 1996).

E. Hammond, "National Committee on Vital and Health Statistics, Subcommittee on Health Data Needs, Standards and Security," http://www.ncvhs.hhs.gov/970211t3.htm, pp. 1-4 (Feb. 11, 1997).

Security and Electronics Signature Standards; Proposed Rule, Federal Register, vol. 63, No. 155 (Aug. 12, 1998).

"Communication pursuant to Article 94(3) EPC, European Examination Report", from the European Patent Office in EP Patent Application No. 06752163.3, corresponding to U.S. Appl. No. 11/121,870, mailed Dec. 10, 2010, (6 pages).

"Response to Japanese Office Action", dated Aug. 8, 2011, Filed in the Japanese Patent Office on Jan. 6, 2012 for Japanese Patent Application No. 2008-510171 corresponding to U.S. Appl. No. 11/121,870, (pp. 19).

"Japanese Office Action", for JP Application No. 2008-510171, corresponding to U.S. Appl. No. 11/121,870, mailed Aug. 30, 2012 (pp. 4) Including English translation.

\* cited by examiner

SYSTEM AND METHOD FOR MANAGING ALERT NOTIFICATIONS IN AN AUTOMATED PATIENT MANAGEMENT SYSTEM

FIELD OF THE INVENTION

The present invention relates in general to automated patient management and, specifically, to a system and method for managing alert notifications in an automated patient management system.

BACKGROUND OF THE INVENTION

Generally, follow-up for patients suffering from chronic medical conditions, such as congestive heart failure or respiratory insufficiency, occurs in-clinic once every three to twelve months, or as necessary. Although mandatory, the clinic visits are also often the only one-on-one interpersonal contact that occurs between the patient and his or her physician or healthcare provider, absent complications or other health-related issues. In-clinic visits allow a clinician to manage those patient medical devices and sensors that may require specific attention, for example, implantable medical devices (IMDs), such as pacemakers or defibrillators, or home-based sensors, such as Holter monitors, although certain patient medical devices and sensors, such as scales and blood pressure cuffs, seldom require clinical follow-up. Where appropriate, devices and sensors are interrogated using a conventional programmer, which retrieves stored event data and device settings and allows reprogramming to modify or upgrade operational behaviors. However, due to limited onboard storage, the patient data received through in-clinic interrogations from the devices and sensors is limited in quantity and represents a "snapshot" of patient wellness, frequently far removed in time from the occurrence of an event of potential medical interest.

Alternative follow-up methods, such as transtelephonic monitoring, can enable a healthcare provider to provide limited remote patient management on a more frequent, often monthly, basis. In addition, dedicated remote patient management devices, such as repeaters, have enabled healthcare providers to remotely perform follow-up monitoring on a daily basis using a data communications network, such as the Internet. Nevertheless, these devices require patients to remember to initiate remote sessions and impose the need to confirm patient data receipt on the clinician. Additionally, substantially all received patient data must be reviewed by a clinician to ensure prudent health care provisioning, which frequently requires specific clinical expertise as a service separate from a general clinical practice.

Therefore, there is a need for an approach to providing automated patient management of remote patients through highly configurable patient data collection and evaluation and alert notification. Preferably, such an approach would relieve clinicians from the drudgery of confirming patient compliance and the routine review of detectable non-critical conditions.

SUMMARY OF THE INVENTION

A system and method includes defining and executing patient data collection and evaluation and alert notifications. Patient data is collected from patient data sources, including implantable and external medical devices and sensors. The patient data can be requested from each patient data source based on a schedule or received asynchronously. The collected patient data is evaluated by the data collection device for a subset of alert conditions and by a server for a complete set of alert conditions. The frequency of evaluation of patient data can be specified as equal to or less than the frequency of collection. Alert notifications are provided when the occurrence of an alert condition triggers a notification scheme. The alert notifications for a common degree of severity can be assigned to alert levels, which can be escalated in succession if the initially selected alert notification goes unacknowledged or if patient data cannot be uploaded to the server.

One embodiment provides a system and method for managing alert notifications in an automated patient management system. One or more settings specifying patient data collection periodicity are defined. One or more patient data sources operating on a remotely managed patient and selected from at least one of a physiological sensor and a therapy delivery device are also defined. One or more triggers associated with a condition occurring in relation to at least one such patient data evaluateable subsequent to collection are defined. Finally, a notification scheme executable upon detection of at least one such trigger is determined to provide an external indicator of the condition occurrence.

Still other embodiments of the present invention will become readily apparent to those skilled in the art from the following detailed description, wherein are described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Automated Patient Management Environment

Figure 1:
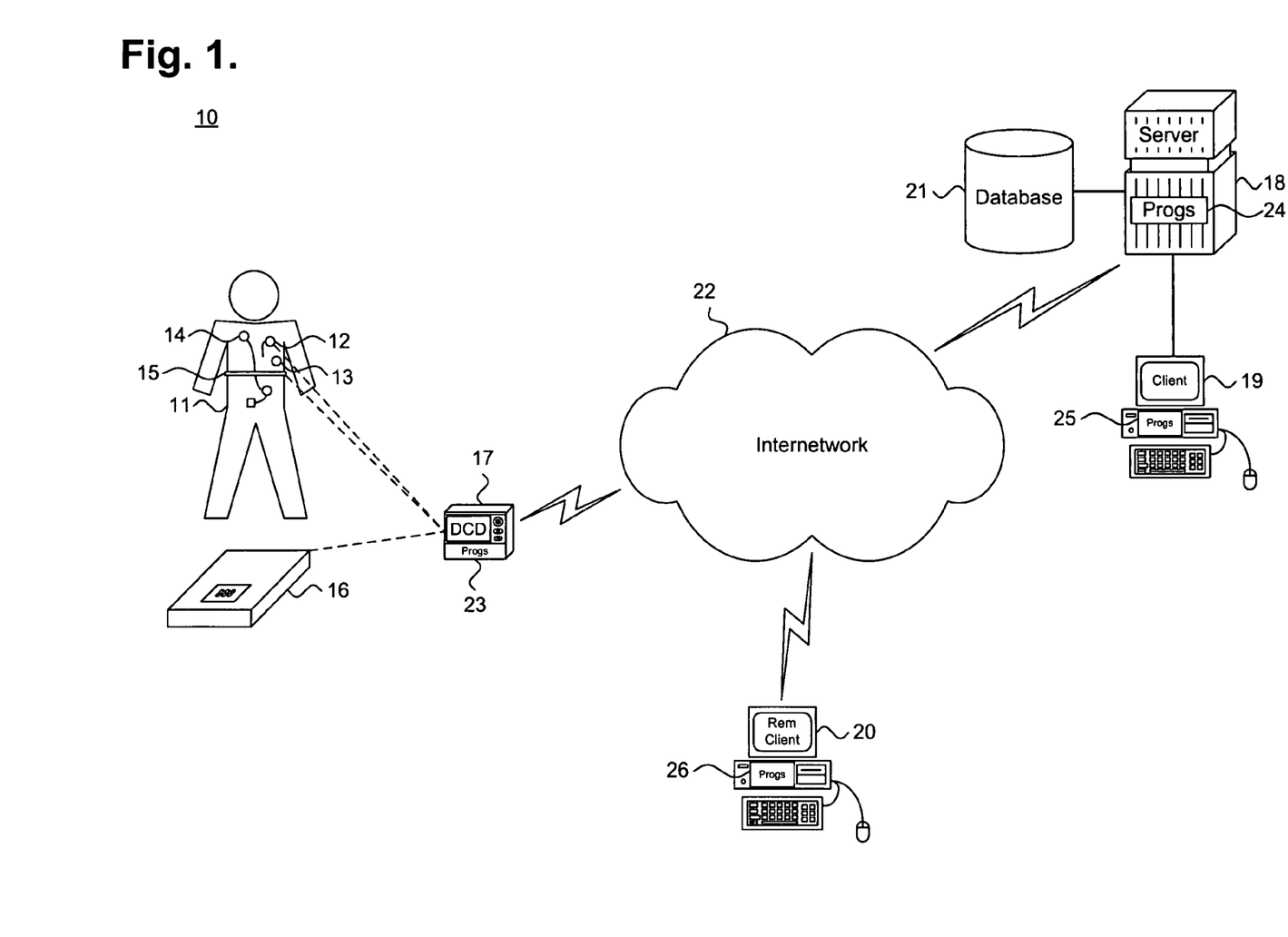
FIG. 1 is a functional block diagram showing, by way of example, an automated patient management environment, in accordance with one embodiment.

Automated patient management encompasses a range of activities, including remote patient management and automatic diagnosis of patient health, such as described in commonly-assigned U.S. Patent application Pub. No. US 2004/0103001, pending, published May 27, 2004, the disclosure of which is incorporated by reference. Such activities can be performed proximal to a patient, such as in the patient's home or office, through a centralized server, such as in a hospital, clinic or physician's office, or through a remote workstation, such as a secure wireless mobile computing device. FIG. 1 is a functional block diagram showing, by way of example, an automated patient management environment 10, in accordance with one embodiment. An individual patient 11 is remotely managed through one or more data collection devices 17, such as repeaters, as further described below with reference to FIG. 10. Each data collection device 17 is interconnected remotely over an internetwork 22, such as the Internet to a centralized server 18, as further described below with reference to FIG. 11. The internetwork 22 can provide both conventional wired and wireless interconnectivity. In one embodiment, the internetwork 22 is based on the Transmission Control Protocol/Internet Protocol (TCP/IP) network communication specification, although other types or combinations of networking implementations are possible. Similarly, other network topologies and arrangements are possible.

Each data collection device 17 is uniquely assigned to an individual patient 11 to provide a localized and network-accessible interface to one or more patient data sources 12-16, either through direct means, such as wired connectivity, or through indirect means, such as inductive, radio frequency or wireless telemetry based on, for example, "strong" Bluetooth or IEEE 802.11 wireless fidelity "WiFi" interfacing standards. Other configurations and combinations of patient data source interfacing are possible.

Patient data includes physiological measures, which can be quantitative or qualitative, parametric data regarding the status and operational characteristics of the patient data source itself, and environmental parameters, such as the temperature or time of day. Other types of patient data are possible. The patient data sources collect and forward the patient data either as a primary or supplemental function. Patient data sources include, by way of example, medical devices that deliver or provide therapy to the patient 11, sensors that sense physiological data in relation to the patient 11, and measurement devices that measure environmental parameters occurring independent of the patient 11. Each patient data source can generate one or more types of patient data and can incorporate one or more components for delivering therapy, sensing physiological data and measuring environmental parameters. In a further embodiment, data values could be entered by a patient 11 directly into a patient data source. For example, answers to health questions could be input into a measurement device that includes interactive user interfacing means, such as a keyboard and display or microphone and speaker. Such patient-provided data values could also be collected as patient information. Additionally, measurement devices are frequently incorporated into medical devices and sensors. Medical devices include implantable medical devices (IMDs) 12, such as pacemakers, implantable cardiac defibrillators (ICDs), drug pumps, and neuro-stimulators, and external medical devices (EMDs) 14, such as automatic external defibrillators (AEDs). Sensors include implantable sensors 13, such as implantable heart and respiratory monitors and implantable diagnostic multi-sensor non-therapeutic devices, and external sensors 15, 16, such as Holter monitors, weight scales, and blood pressure cuffs. Other types of medical, sensing, and measuring devices, both implantable and external, are possible.

The data collection device 17 collects and temporarily stores patient data from the patient data sources 12-16 for periodic upload over the internetwork 22 to the server 18 and storage in a database 21. Patient data collection can be defined to be initiated by either the patient collection device 17 or by one or more of the patient data sources 12-16, as further described below with reference to FIGS. 4 and 5.

In a further embodiment, the collected patient data can also be accessed and analyzed by one or more locally-configured clients 19 or one or more remote clients 20 securely-interconnected over the internetwork 22. The clients 19 and remote clients 20 can be used, for example, by clinicians, such as physicians, nurses, or qualified medical specialists, to securely access stored patient data assembled in the database 21 and to select and prioritize patients for health care provisioning, such as respectively described in commonly-assigned U.S. patent application, entitled, "System and Method for Managing Coordination of Assembled Patient Data in an Automated Patient Management System," Ser. No. 11/121, 593, filed May 3, 2005, pending, and U.S. patent application, entitled, "System and Method for Managing Patient Triage in an Automated Patient Management System," Ser. No. 11/121, 594, filed May 3, 2005, pending, the disclosures of which are incorporated by reference. Although described herein with reference to clinicians, the entire discussion applies equally to organizations, including hospitals, clinics, and laboratories, and other individuals or interests, such as researchers, scientists, universities, and governmental agencies, seeking access to the patient data.

The collected patient data can also be evaluated for the occurrence of one or more conditions, such as described in related, commonly-owned U.S. Pat. No. 6,336,903, to Bardy, issued Jan. 8, 2002; U.S. Pat. No. 6,368,284, to Bardy, issued Apr. 9, 2002; U.S. Pat. No. 6,398,728, to Bardy, issued Jun. 2, 2002; U.S. Pat. No. 6,411,840, to Bardy, issued Jun. 25, 2002; and U.S. Pat. No. 6,440,066, to Bardy, issued Aug. 27, 2002, the disclosures of which are incorporated by reference. Patient data evaluation can be defined to be performed by either the patient collection device 17 or the server 18, as further described below with reference to FIGS. 6 and 7.

Finally, conditions occurring in the collected patient data can trigger one or more alert notifications that provide external indicators of the condition occurrences. Alert notification can be defined to be performed by either the server 18, patient collection device 17, or one or more other devices either operating as part of or as an adjunct to the internetwork 22, as further described below with reference to FIGS. 8 and 9.

In a further embodiment, patient data is safeguarded against unauthorized disclosure to third parties, including during collection, assembly, evaluation, transmission, and storage, to protect patient privacy and comply with recently enacted medical information privacy laws, such as the Health Insurance Portability and Accountability Act (HIPAA) and the European Privacy Directive. At a minimum, patient health information that identifies a particular individual with health- and medical-related information is treated as protectable, although other types of sensitive information in addition to or in lieu of specific patient health information could also be protectable.

Preferably, the server 18 is a server-grade computing platform configured as a uni-, multi- or distributed processing system, and the clients 19 and remote clients 20 are general-purpose computing workstations, such as a personal desktop or notebook computer. In addition, the data collection device 17, server 18, clients 19, and remote clients 20 are programmable computing devices that respectively execute set of software programs 23, 24, 25, 26 and include components conventionally found in computing device, such as, for example, a central processing unit (CPU), memory, network interface, persistent storage, and various components for interconnecting these components.

Options Definition

Figure 2:
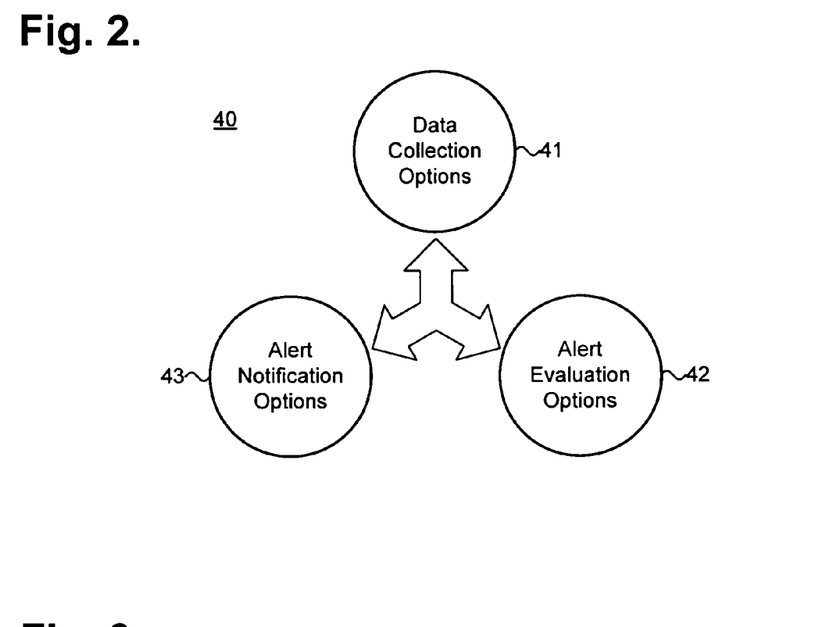
FIG. 2 is a process flow diagram showing options definition in the environment of FIG. 1.

Managing alert notifications requires collecting patient data, evaluating collected patient data, and providing alert notifications if an alert condition is triggered. Each of these operations can be configured to customize the alert notifications to the specific needs of each patient. FIG. 2 is a process flow diagram showing options definition 40 in the environment 10 of FIG. 1. In one embodiment, options can be defined for data collection 41, alert evaluation 42, and alert notification 43 using the data collection device 17, server 18, clients 19, and remote clients 20, depending upon the type and nature of the particular option being defined. For instance, certain options, such as an alert notification that an implanted device battery is nearing an end-of-life condition, are immutable and cannot be changed. Other options, such as the frequency with which collected data is evaluated, are default options that can be modified if the initial configuration requires change.

The setting of data collection options 41 can involve a data collection device 17, the server 18, and the patient data sources 12-16 interfaced to the data collection device 17. Patient data can be collected at the initiative of either the data collection device 17 or one or more of the patient data sources, as further described below with reference to FIG. 4.

The setting of alert evaluation options 42 can involve a data collection device 17 or the server 18. Patient data collected by each data collection device 17 is uploaded to the server 18. Upon receiving new patient data, a data collection device 17 can be configured to evaluate the patient data for a subset of alert conditions and to collect additional patient data if an enabled alert condition is detected and the server 18 can be configured to evaluate the patient data for a complete set of alert conditions, as further described below with reference to FIG. 6.

The setting of alert notification options 43 can involve a data collection device 17 and the server 18. If one or more alert conditions are detected, a data collection device 17 or the server 18 can be configured to trigger an alert notification, as further described below with reference to FIG. 8. In a further embodiment, default alert levels can be assigned to alert notifications that are each triggered upon the detection of condition having increasing degrees of severity. Accordingly, a condition of minor severity could have a moderate alert level, whereas a condition of significant severity could have a high alert level. In addition, alert notifications for a common degree of severity can be escalated through successive alert levels if the initially selected alert notification goes unacknowledged or if patient data cannot be uploaded to the server.

In one embodiment, to manage the complexity that a wide variety of configuration options provide, configuration option default settings can be provided using the following default setting groups, which may each have an associated defined set of degrees of severity:

System-wide: provides configuration option values that are factory-provided as the initial values for a configurable parameter.

Subpopulation-specific: provides configuration option values that are defined for specific patient groups. For example, Class III-IV Heart Failure patients may require conditions to be monitored that a standard pacemaker patient would not. This level includes system-wide default settings customized to a patient subpopulation and can also include alert notifications arising out of guidelines issued by organizations like HRS, ACC, HFSA, AHA, and AMA.

User-specified default settings for all patients: provides configuration options values as custom default values defined by a clinician to be applied to all of their patients.

User-specified default settings for custom groupings of patients: provides configuration options as sets of custom default values defined by a clinician to be applied to a custom patient grouping. This level may involve the customization of subpopulation-specific default configuration option values.

Other configuration option default settings are possible.

In a further embodiment, only select configuration options are available at all levels. For example, battery depletion or device failure conditions may be system-wide default configuration options that are non-user modifiable. In contrast, a percentage pacing alert condition may be disabled as a system-wide default configuration option, but can be enabled for certain patient populations where pacing is required, such as for resynchronization patients.

Options Usage

Figure 3:
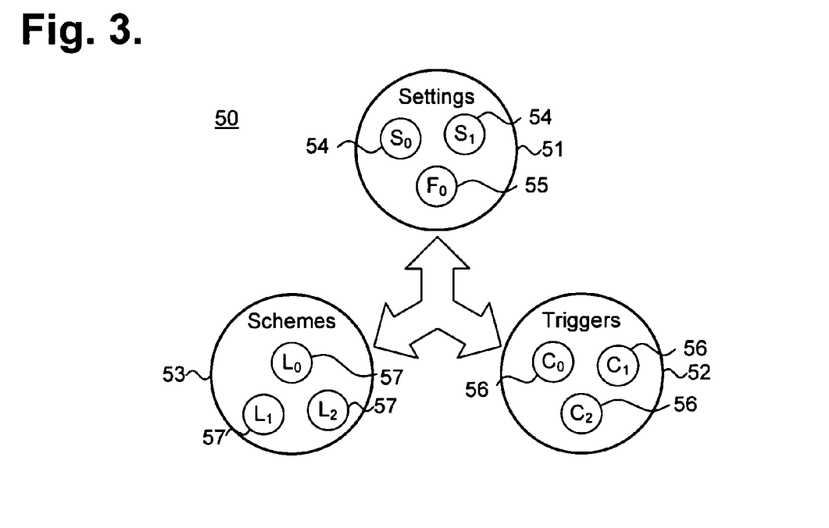
FIG. 3 is a data flow diagram showing options defined for use in the environment of FIG. 1.

Generally, options can only be defined by an authorized clinician, such as a physician, nurse, or qualified medical specialist. FIG. 3 is a data flow diagram showing options 50 defined for use in the environment 10 of FIG. 1. The options for data collection, alert evaluation, and alert notification are respectively grouped into settings 51, triggers 52, and schemes 53.

Settings 51 specify data collection periodicity for the patient data sources 12-16, which are interfaced to a particular data collection device 17. Settings 51 include schedules 54 and frequencies 55 that can be associated with one or more patient data sources. Schedules 54 allow a data collection device 17 to periodically request and receive, or "pull," patient data from the associated patient data source. Frequencies 55 allow a data collection device 17 to track or limit the receipt of patient data from patient data sources that autonomously send, or "push," patient data to the data collection device 17. Limiting the receipt of patient data can help moderate and control excessive usage of a patient data source, particularly by an overly-compulsive patient. Other types of settings are possible.

Triggers 52 associate the occurrence of an alert condition 56 with an alert notification scheme 53. An alert condition 56 can set off one or more triggers 52 and the type of alert condition 56 depends upon the nature of the patient data. Other types of triggers are possible.

Schemes 53 are executed to provide an alert notification upon the detection of an associated trigger 52, which is an external indicator of an alert condition. Alert notifications can be provided to the patient, clinician, or third parties. In a further embodiment, the schemes 53 can be arranged into alert levels 57. A set of default alert levels 57 can be assigned to a corresponding set of alert notifications that are each triggered upon the detection of the conditions having increasing degrees of severity. Additionally, multiple alert levels 57 can also be assigned to one or more individual alert notifications and the alert notifications are progressively escalated through the alert levels if, for instance, the initially selected alert notification goes unacknowledged or if patient data cannot be uploaded to the server. In a still further embodiment, an alert notification is only provided only upon an initial detection of a condition to ensure that the same alert notification is not continuously resent each time a new set of patient data is received. Other types of schemes are possible.

Data Collection Option Definition

Figure 4:
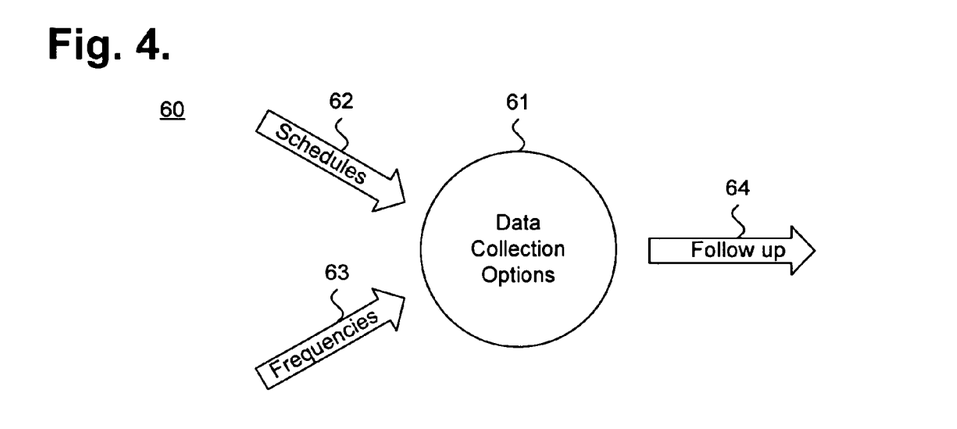
FIG. 4 is a process flow diagram showing data collection option definition in the environment of FIG. 1.

Data collection primarily involves the receipt of patient data into a data collection device 17. FIG. 4 is a process flow diagram showing data collection option definition 60 in the environment 10 of FIG. 1. Data collection can be configured to be initiated by one or more of the patient data sources 12-16, the data collection device 17, or both. Data collection options can be defined by clinician using the server 18 or, in a further embodiment, a client 19 or remote client 20.

In one embodiment, the following configuration options 61 are provided for patient data sources configured to provide scheduled data collection:

Schedule frequency 62: defines the periodicity of patient data collection, including 24-hour/7-days per week monitoring.

Response to lack of communication with the patient data source 64: defines operations to take for a non-responding patient data source as a follow-up, including when to retry or to communicate failure to the server, or to send a message or other communication to the patient 11, clinician or authorized third party as a compliance notification.

Other schedule configuration options are possible.

In one embodiment, the following configuration options 61 are provided for patient data sources configured to provide asynchronous data collection:

Maximum frequency 63: defines the intervals at which the data collection device should accept data from a patient data source, including limiting data collection.

Response to lack of communication with the patient data source 64: defines operations to take for a non-responding patient data source as a follow-up, including when to retry or to communicate failure to the server, or to send a message or other communication to the patient 11, clinician or authorized third party as a compliance notification.

Other frequency configuration options are possible.

Generally, the data collection device 17 can be configured to immediately upload collected patient data to the server 18. In a further embodiment, a maximum delay can be specified to allow the patient data collected from multiple patient data sources to be uploaded in a single call to the server 18, which might be more cost effective depending upon the connection means used.

Data Collection Option Execution

Figure 5:
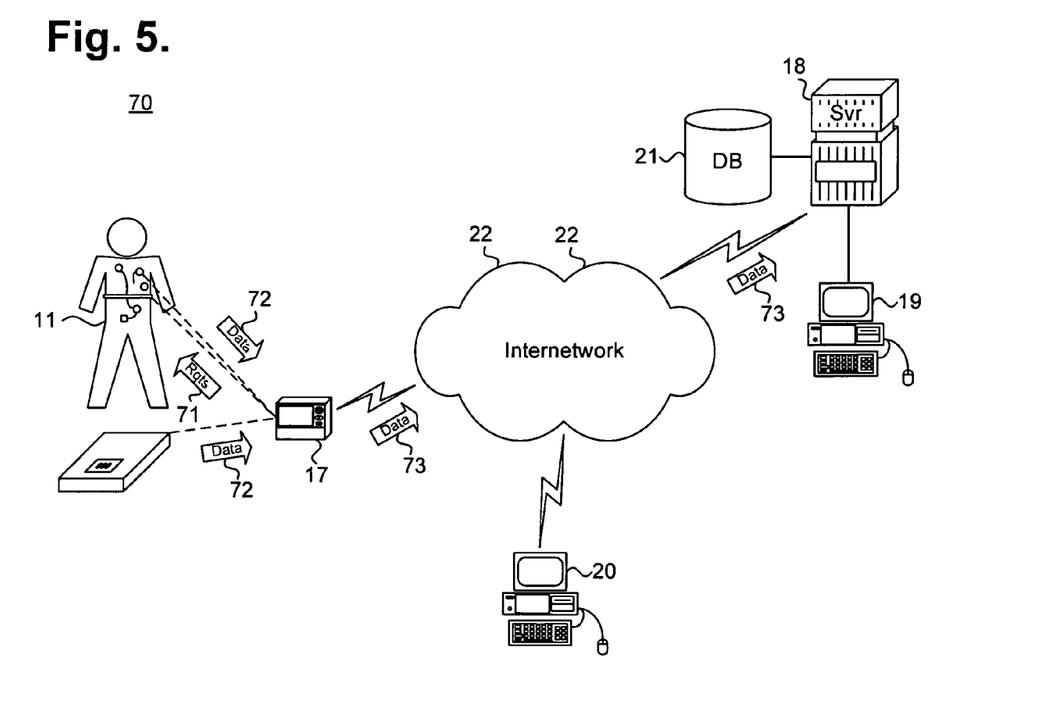
FIG. 5 is a functional block diagram showing data collection option execution in the environment of FIG. 1.

Automated patient management allows a potentially enormous amount of patient data to be generated through substantially continuous monitoring and the amount and frequency of such patient data generation can be controlled through the data collection options 61. FIG. 5 is a functional block diagram showing data collection option execution 70 in the environment 10 of FIG. 1. The execution reflects the dichotomy of data collection device-versus patient data source-initiated data collection.

Patient data sources that operate autonomously from the patient are generally able to record patient data at any time and under any conditions. However, the recorded patient data accumulated by the patient data source must be periodically uploaded to free limited onboard storage and to facilitate processing and analysis. Schedules 62 are associated with a subset of the interfaced patient data sources to provide data collection device-initiated patient data collection. Alternatively, a schedule can also be provided to initiate prompted retrieval of patient data by the remotely managed patient. A schedule 62 might be appropriate for a patient data source, such as an implanted cardiac pulse generator, where patient data may be collected on a daily or weekly basis. The schedule 62 can either be built into the data collection device 61 or can be provided by the server 18, based on configuration options selected by the clinician. The data collection device 61 attempts to collect patient data at a scheduled interval by sending requests 71 to the associated patient data source, which returns patient data 72. In the absence of expected patient data receipt, the data collection device 61 can implement a follow-up scheme 64 with the patient data source, if possible, to investigate delayed or missing patient data, or by sending a message or other communication to the patient 11, clinician or authorized third party as a compliance notification.

Scheduled data collection might not be appropriate for all patient data sources 12-16. For example, a battery powered weight scale that uses radio frequency telemetry to communicate with a data collection device 17 would normally be turned off to extend battery life. Ordinarily, such a device would communicate with the data collection device 17 only after use by the patient and would otherwise be in a standby or sleep state. Such devices frequently operate in a send-only mode and may therefore be incapable of receiving incoming messages. The patient data source asynchronously sends patient data 72 to the data collection device 17 to provide patient data source-initiated patient data collection. Frequencies 63 are associated with a subset of the interfaced patient data sources to allow the data collection device 17 to track or limit the receipt of patient data. In the absence of expected patient data receipt, the data collection device 61 can implement a follow-up scheme 64 with the patient data source, if possible, to investigate delayed or missing patient data or excessive patient data delivery, or by sending a message or other communication to the patient 11, clinician or authorized third party as a compliance notification.

Finally, collected patient data 73 is uploaded by the data collection device 17 to the server 18 either upon receipt or, in a further embodiment, after a delay to allow patient data 72 from multiple patient data sources to accumulate. The server 18 stores the uploaded patient data 73 in the database 21.

Alert Evaluation Option Definition

Figure 6:
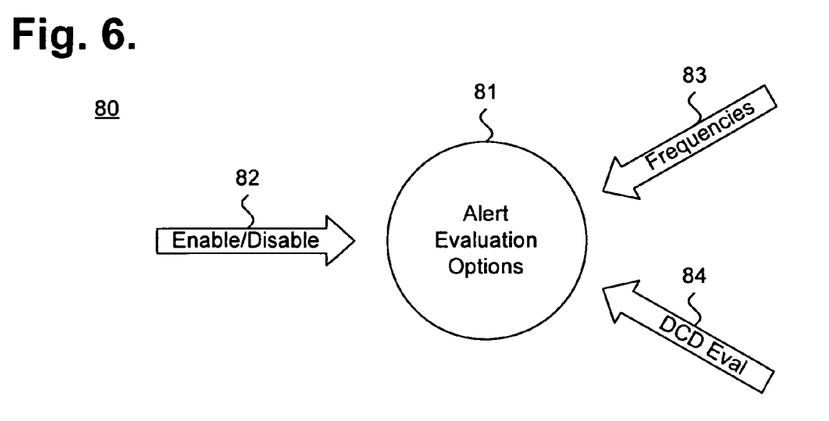
FIG. 6 is a process flow diagram showing alert evaluation option definition in the environment of FIG. 1.

Alert evaluation can be configured to be performed by a data collection device or the server. FIG. 6 is a process flow diagram showing alert evaluation option definition 80 in the environment 10 of FIG. 1. Alert evaluation options can be defined by clinician using the server 18 or, in a further embodiment, a clients 19 or remote client 20.

In one embodiment, the following configuration options 81 are provided for alert evaluation:

Enable/disable 82: defines whether an alert condition is evaluated. Certain alert rules may not be disabled, particularly those alert conditions that are defined at a "Red" or maximum alert level.

Frequency of evaluation 83: defines how often an alert condition is evaluated. By default, patient data is evaluated immediately upon collection. However, the evaluation frequency can be configured to be less than the collection frequency.

Whether the alert check should be performed in the data collection device 84: defines a range of the alert conditions that are to be evaluated by the data collection device. In addition, an alert check that is performed in the data collection device could also trigger further patient data collection.

Other alert evaluation options are possible.

Alert Evaluation Option Execution

Figure 7:
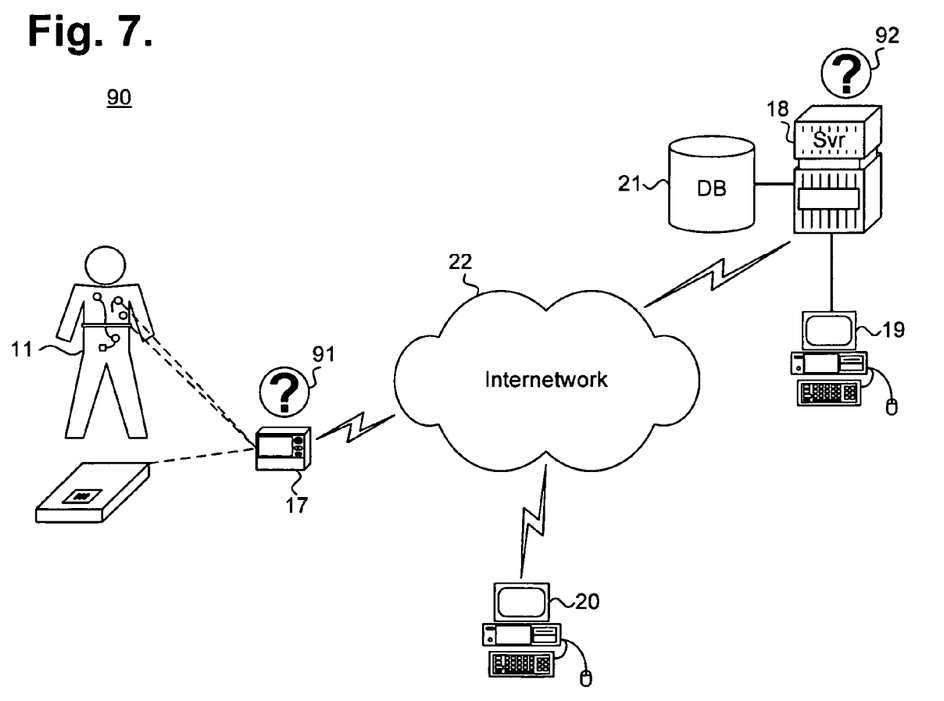
FIG. 7 is a functional block diagram showing alert evaluation option execution in the environment of FIG. 1.

Collected patient data must be evaluated to detect the occurrence of an alert condition. FIG. 7 is a functional block diagram showing alert evaluation option execution 90 in the environment 10 of FIG. 1. Alert evaluation can be performed either as data collection device-based evaluation 91, as a subset of the alert conditions, or as server-based evaluation 92, over the full set of alert conditions. The same alert conditions can be evaluated by both the data collection device 17 and the server 18 and, in a further embodiment, the server 18 can perform a comprehensive evaluation based on collected patient data stored in the database 18.

In one embodiment, the following types of alert conditions are evaluated:
  Battery level low.
    End of life.
    Early replacement indicated.
    Excessive battery use, including whether the rate of battery depletion above an expected threshold.
  Tachycardia therapy disabled.
    Tachycardia mode monitor only.
    Tachycardia mode off.
    Magnet mode therapy disable.
  Implanted lead conditions.
    Defibrillation lead conditions.
    Pacing lead conditions.
  Pacing capture conditions.
    Loss of capture.
    Safety margin too low.
  Pacing percentage above or below an expected range.
  Tachycardia therapy conditions.
    Tachycardia therapy delivered to convert arrhythmia.
    Tachycardia therapy accelerated arrhythmia.
    Tachycardia therapy exhausted.
  Atrial conditions.
    Time in Atrial Fibrillation exceeding a threshold.
    Time in Atrial Flutter exceeding a threshold.
    Atrial therapy delivered.
  Activity level above or below a threshold.
  Heart rate variability below a threshold.
  Maximum heart rate above a threshold.
  Weight increase or decrease.
  Blood pressure, including systolic, diastolic, or mean arterial pressures, above or below a threshold.
  Blood sugar above or below a threshold.
  Apnea index above a threshold.
  Device failure, including implanted and external devices.
  Patient triggered event.
  Oxygen Saturation below a threshold.
  Implanted sensor information.
    Cardiac output below a threshold.
    Pulmonary artery pressure above or below a threshold.
    Pulmonary edema level above a threshold.
Other types of alert conditions are possible.

Alert Notification Option Definition

Figure 8:
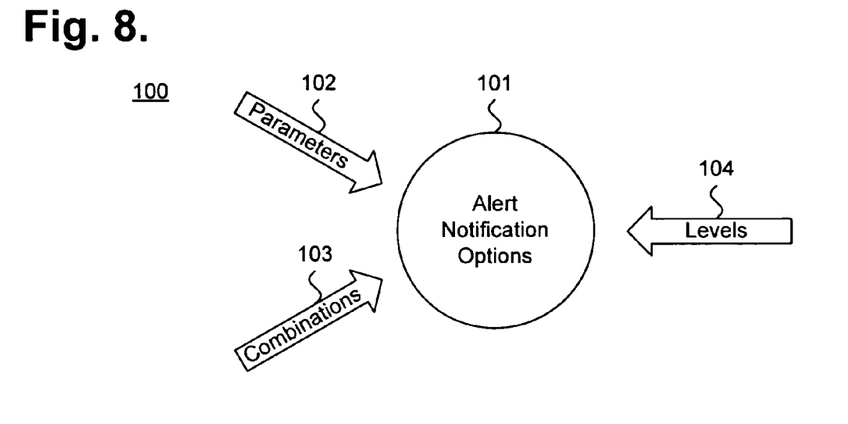
FIG. 8 is a process flow diagram showing alert notification option definition in the environment of FIG. 1.

Alert notifications can be provided to the patient, clinician, or third parties, depending upon the type and nature of the underlying alert condition, as well as patient privacy considerations. FIG. 8 is a process flow diagram showing alert notification option definition 100 in the environment 10 of FIG. 1. Alert notification options can be defined by clinician using the server 18 or, in a further embodiment, a client 19 or remote client 20.

In one embodiment, the following configuration options 101 are provided for alert definition:
  Parameters 102: defines whether an alert condition may be provided with configurable parameters. For example, a lead impedance alert condition may have programmable impedance levels, a weight alert condition may have a programmable weight change, and a pacing percentage alert condition may have a percentage paced parameter.
  Combinations 103: defines whether custom alerts can be created by combining alert conditions with Boolean logic operations, such as "AND," "OR" and "NOT" operations. Other Boolean logic and alert condition aggregating operations are possible.
  Alert levels 104: defines whether the alert level of an alert condition may be configured. In one embodiment, default alert levels of "Red" and "Yellow" are provided, but additional levels may be created. The default alert levels assigned to immutable alert conditions are not be permitted to be changed. For example, an implanted device battery nearing an end-of-life condition may not be changed from a default "Red" alert condition.
Other alert notification options are possible.

In a further embodiment, if an alert condition is present, yet was not present the last time that the alert condition was evaluated, an alert notification may be generated to communicate the presence of the alert condition to the clinician, patient, or both.

In a still further embodiment, responses to alert notifications are monitored and analyzed as a form of self-directed learning. The responses are evaluated, for instance, to identify patterns and consistent behaviors, which can then be used to modify future alert notifications. For example, where a clinician consistently responds to a particular type of alert notification by dismissing the notification, subsequent alert notifications of the same type could append a prompt to ask the clinician if the alert notification should be disabled. Other types of response monitoring and analysis are possible.

Alert Notification Option Execution

Figure 9:
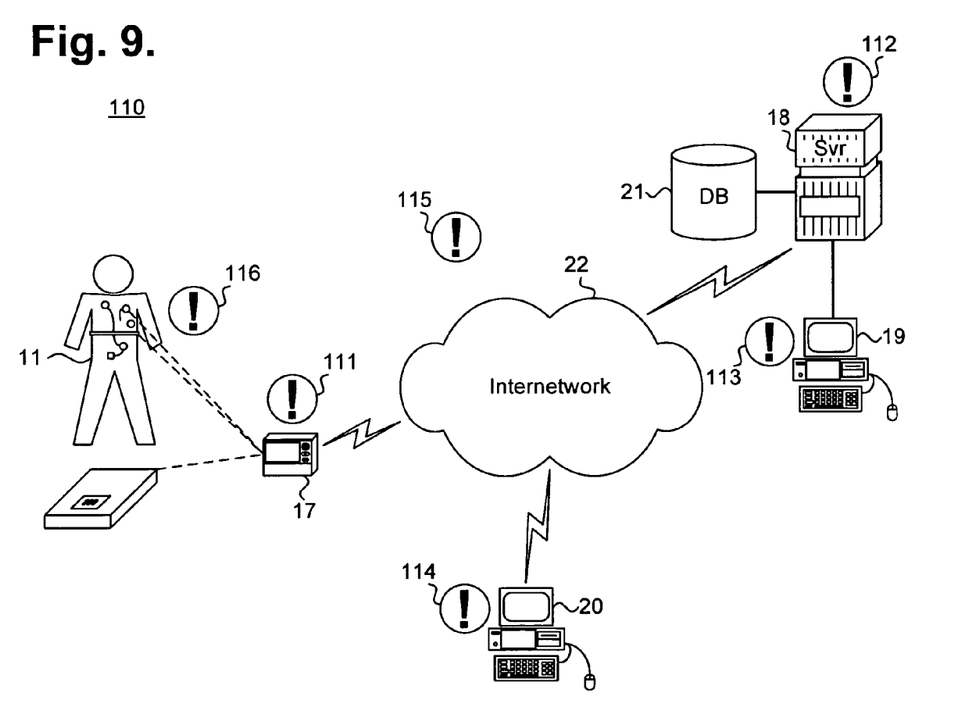
FIG. 9 is a functional block diagram showing alert notification option execution in the environment of FIG. 1.

Alert notifications provide the means by which the presence of a new alert condition is communicated to a patient, clinician, or third parties. FIG. 9 is a functional block diagram showing alert notification option execution 110 in the environment 10 of FIG. 1. Alert notifications are associated with the alert levels 104 and, by default, all alert notifications at a particular level share the same means for notification. Alert notifications can be provided to a clinician or authorized third party at a data collection device 111, the server 112, a client 113, and a remote client 114, and via external communications means 115, and to the patient via external communications means 116.

In one embodiment, the following types of alert notifications are provided:
  Notification means: defines the primary mechanism by communications media and conduit over which the alert notification is sent.
    Web page update.
    Phone call, including automated or manual.
    Pager call.
    E-mail.
    SMS or text message to a personal data assistant, cellular telephone, or similar device.
    "Instant Message" to a computer.
    Data collection device 17 message to the patient.
    Simultaneous direct notification to emergency services and to the clinician.
  Escalation mechanism: defines the secondary mechanism that is used if the primary mechanism fails, plus the amount of time that is allowed to lapse before the secondary mechanism is invoked. Tertiary and successive mechanisms are possible.
Other alert notifications are possible.

Data Collection Device

Figure 10:
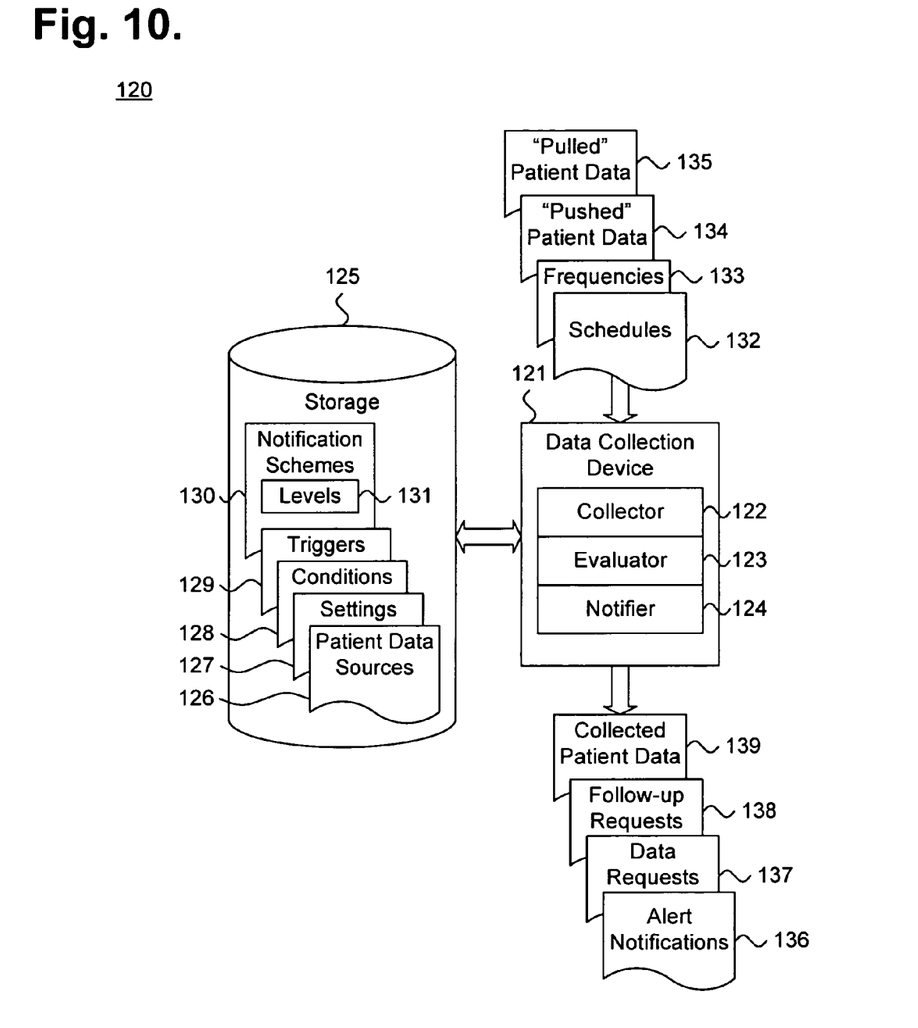
FIG. 10 is a functional block diagram showing a patient management device for managing alert notifications in an automated patient management system for use in the environment of FIG. 1.

Each data collection device acts as the central hub for the remote management of individual patients. FIG. 10 is a functional block diagram 120 showing a patient management device 121 for managing alert notifications in an automated patient management system for use in the environment 10 of FIG. 1. The data collection device 121 includes a storage 125 and can be configured to collect patient data, evaluate collected patient data, and provide alert notifications. Other data collection device functions are possible.

The data collection device 121 includes a collector 122, evaluator 123, and notifier 124. The collector 122 maintains a list of devices and sensors 126 for interfaced patient data sources 12-16 and collects patient data based on collection periodicity settings 127. The collector 122 actively collects "pulled" patient data 135 received from the patient data sources 12-16 based on schedules 132. Pulled patient data collection is initiated by sending a data request 137 to the associated patient data source. The collector 122 also passively receives "pushed" patient data asynchronously sent from the patient data sources 12-16. The collector 122 keeps track of pushed patient data collection by monitoring frequencies 133. The collector 122 can execute a follow-up scheme, for example, by sending follow-up requests 138 to patient data sources, if possible, that have not sent expected patient data, or by sending a message or other communication to the patient 11, clinician or authorized third party as a compliance notification. Finally, the collector 122 uploads the collected patient data 139 to the server 18, either upon receipt or after a maximum delay to allow patient data to accumulate.

The evaluator 123 evaluates both the "pushed" patient data 134 and the "pulled" patient data 135 against a subset of alert conditions 128. One or more triggers 129 are associated with the alert conditions 128 and occurrences of alert condition 128 set off the associated triggers 129. In addition, an alert condition 128 could also trigger further patient data collection. The same alert conditions 128 can be evaluated by both the data collection device 121 and the server.

The notifier 124 provides alert notifications 136. Alert notifications 136 are assigned to notification schemes 130 that are executed upon the detection of an associated trigger 129. The notification schemes 130 can be organized into one or more levels 131 of alerts.

Server

Figure 11:
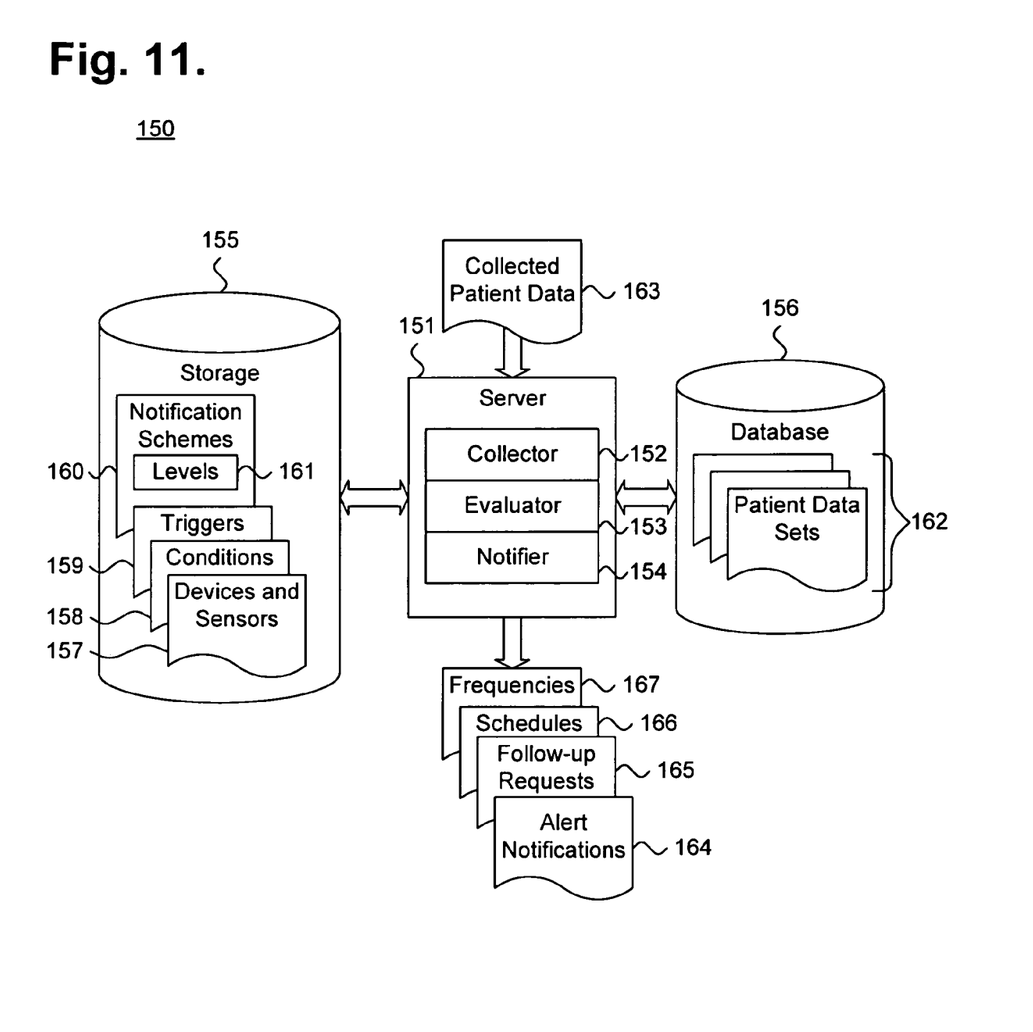
FIG. 11 is a functional block diagram showing a server for managing alert notifications in an automated patient management system for use in the environment of FIG. 1.

The server acts as the central hub for collected patient data storage and analysis. FIG. 11 is a functional block diagram 150 showing a server 151 for managing alert notifications in an automated patient management system for use in the environment 10 of FIG. 1. The server 151 includes storage 155 and database 156 and can be configured to evaluate collected patient data and provide alert notifications. Other server functions are possible.

Similar to the data collection device 121, the server 151 includes a collector 152, evaluator 153, and notifier 154. The collector 152 maintains a list of devices and sensors 157 for all patient data sources 12-16, which can be used by a clinician to create schedules 166 and maximum frequencies 167 to manage the collection of patient data by interfaced data collection devices 121. The collector 152 collects patient data 163 received from the data collection devices 121, which are stored as patient data sets 162 in the database 156. The collector 152 can execute a follow-up scheme by sending follow-up requests 165 to data collection devices 121, if possible, that have not sent expected collected patient data, or by sending a message or other communication to the patient 11, clinician or authorized third party as a compliance notification.

The evaluator 153 evaluates the collected patient data 163 against a complete set of alert conditions 158. One or more triggers 159 are associated with the alert conditions 158 and occurrences of alert condition 158 set off the associated triggers 159. The same alert conditions 158 can be evaluated by both the server 151 and data collection devices 121.

The notifier 154 provides alert notifications 164. Alert notifications 164 are assigned to notification schemes 160 that are executed upon the detection of an associated trigger 159. The notification schemes 160 can be organized into one or more levels 161 of alerts. By way of example, alert notifications 164 can include a Web page update, phone or pager call, E-mail, SMS, text or "Instant" message, as well as a message to the patient send through the data collection device 17 and simultaneous direct notification to emergency services and to the clinician. Other alert notifications are possible.

While the invention has been particularly shown and described as referenced to the embodiments thereof, those skilled in the art will understand that the foregoing and other changes in form and detail may be made therein without departing from the spirit and scope of the invention.

What is claimed is:

1. A system for managing alert notifications in an automated patient management system, comprising:
a server for patient data storage and analysis, wherein the server comprises a server collector configured to manage collection of patient data by one or more data collection devices, a server evaluator configured to evaluate collected patient data against a complete set of alert conditions, and a server notifier configured to provide alert notifications when an alert condition is detected, wherein the complete set of alert conditions comprises user configurable alert conditions and user non-configurable alert conditions; and
one or more data collection devices uniquely assigned to an individual patient; the one or more data collection devices comprising a device collector configured to receive patient data for the individual patient from one or more patient data sources selected from at least one implantable medical device and at least one external physiological data sensor, a device evaluator for evaluating patient data against a subset of the alert conditions, and a device notifier configured to provide an alert notification when an alert condition is detected, wherein the subset of the alert conditions comprises user configurable alert conditions and user non-configurable alert conditions.

2. The system of claim 1, wherein the data collection device is configured to collect additional patient data when an alert condition is met.

3. The system of claim 1, wherein the set of alert conditions includes default alert conditions.

4. The system of claim 3, wherein the default alert conditions include system-wide defaults, subpopulation specific defaults, user-specified for all patients defaults, and user-specified for custom groupings of patients defaults.

5. The system of claim 1, wherein the server collector is configured to issue one or more follow up requests to one or more data collection devices when an alert condition is detected.

6. The system of claim 1, wherein the device collector is configured to implement a follow-up scheme when patient data is not received.

7. The system of claim 1, wherein the server collector maintains a list of devices and sensors for all patient data sources.

8. A method of managing alert notifications in an automated patient management system comprising:
defining one or more settings specifying patient data collection periodicity;

defining a set of alert conditions comprising user configurable alert conditions and user non-configurable alert conditions;

collecting patient data from at least one implantable medical device and at least one external physiological sensor with a data collection device uniquely assigned to an individual patient;

evaluating the patient data against a subset of the alert conditions with the data collection device, wherein the subset of the alert conditions comprises at least one of the user configurable alert conditions and at least one of the user non-configurable alert conditions;

transferring the patient data to a server;

evaluating the patient data against the set of alert conditions comprising user configurable alert conditions and user non-configurable alert conditions with the server, and issuing an alert notification when one or more alert conditions are met.

9. The method of claim 8, further comprising collecting additional patient data with the data collection device when an alert condition is met.

10. The method of claim 8, wherein the set of alert conditions includes default alert conditions.

11. The method of claim 10, wherein the default alert conditions include system-wide defaults, subpopulation specific defaults, user-specified for all patients defaults, and user-specified for custom groupings of patients defaults.

12. The method of claim 8, further comprising executing a notification scheme with the data collection device when an alert condition is met.

13. The method of claim 8, further comprising executing a notification scheme with the server when an alert condition is met.

14. The method of claim 8, further comprising executing a follow-up scheme with the data collection device when patient data is not received by the data collection device.

15. The method of claim 8, further comprising maintaining a list on the server of devices and sensors for all patient data sources.

16. The method of claim 8, wherein the alert notification can be dismissed and dismissal of the alert notification results in a prompt to disable the alert notification.

17. The system of claim 1, wherein the device collector is configured to issue one or more follow up requests to one or more patient data sources when an alert condition is detected.

* * * * *